United States Patent [19]

Hall

[11] 4,050,464
[45] Sept. 27, 1977

[54] SURGICAL CABLE TENSIONING INSTRUMENT

[75] Inventor: John Emmett Hall, Boston, Mass.

[73] Assignee: Downs Surgical Limited, Mitcham, England

[21] Appl. No.: 680,235

[22] Filed: Apr. 26, 1976

[30] Foreign Application Priority Data

Apr. 28, 1975    United Kingdom ............... 17613/75

[51] Int. Cl.² .................. A61B 17/00; A61F 5/00
[52] U.S. Cl. ........................ 128/303 R; 128/69;
           128/92 E; 81/302; 29/268
[58] Field of Search ............ 128/69, 78, 83, 92 R,
      128/92 B, 92 E, 92 EA, 303 R, 321, 334 R;
                            81/302; 29/239, 268

[56] References Cited

U.S. PATENT DOCUMENTS 2,291,413   7/1942   Siebrandt ........................... 128/83

OTHER PUBLICATIONS

"Harris Wire Knot Tightener" Advertisement, p. 66, Downs Surgical, Inc., The Journal of Bone & Joint Surgery, vol. 50-A, No. 3, Apr. 1968.
"Harris' Wire Knot Tightener" (G520), *Orthopaedic Catalogue*, Down Bros. & Mayer & Phelps Ltd, p. G67.

*Primary Examiner*—Ronald L. Frinks
*Attorney, Agent, or Firm*—Haight & Huard

[57] ABSTRACT

Surgical instrument for applying tension to a metal cable secured to the spine in an operation for the correction of scoliosis.

13 Claims, 6 Drawing Figures

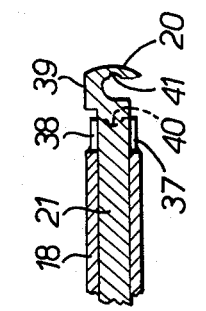
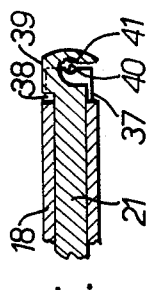
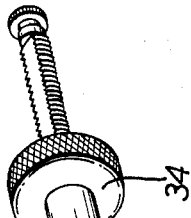
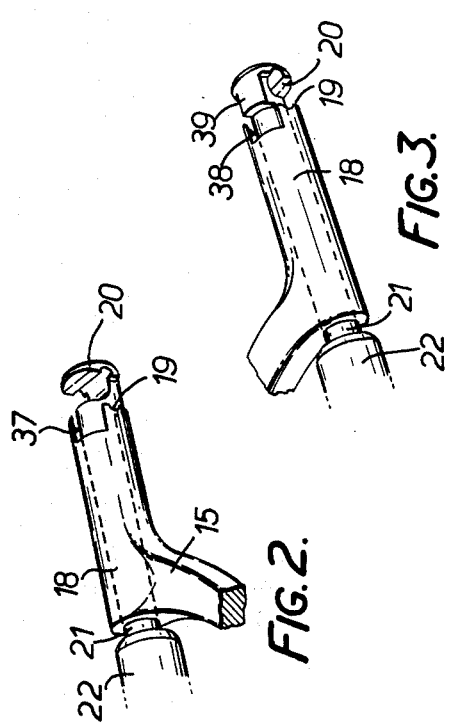
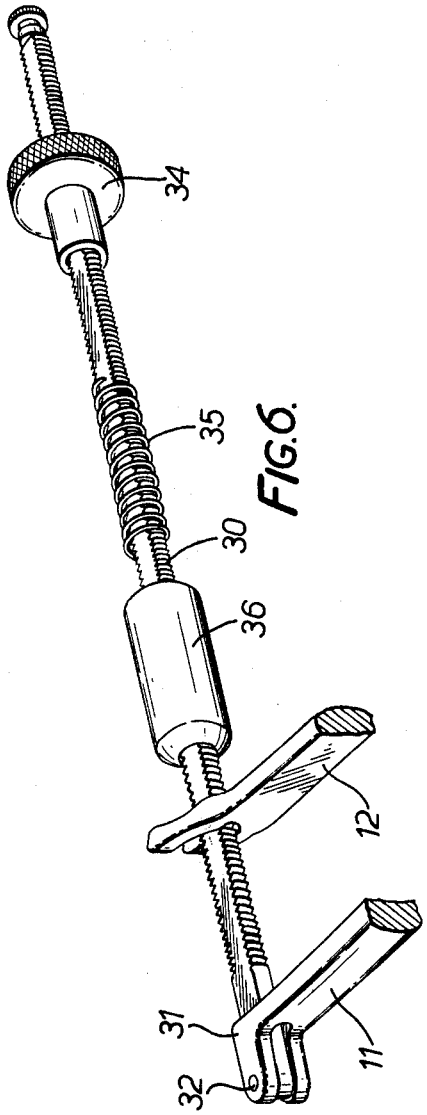

SURGICAL CABLE TENSIONING INSTRUMENT

This invention relates to a surgical instrument for use in the correction of curvature of the spinal column.

One technique that is used for the correction of spinal curvatures is the Dwyer technique of anterior instrumentation of the spine; (c.f. A. F. Dwyer, "Anterior approach to scoliosis," *Journal of the Western Pacific Orthopaedic Association,* Vol. VI, No. 1, Mar. 1969; A. F. Dwyer et al, "Anterior approach to scoliosis," *Clinical Orthopaedics and Related Research,* No. 62, pp. 192 - 202, 1969; and A. F. Dwyer, "Anterior approach to scoliosis," ibid, No. 93, July 1973). This technique involves operation on the front of the spine, with access to the spine being gained by the removal of one rib, or possibly of two ribs. This method may be used for the correction of scoliosis (lateral curvature of the spinal column) when posterior elements are absent, such as in myelomeningocele or after an extensive laminectomy. It is particularly useful when lordosis (curvature of the spinal column with a forward convexity) is associated with scoliosis, and can often be used as a supplementary means of fixation in very long paralytic curves, especially those associated with lordosis in the lumbar region.

The technique involves the application of compression on the convex side of the spinal curve, after the contents of the discs have been excised, so as to straighten the curve. The compression is applied by means of a metal cable threaded through the heads of screws, one of which is anchored through a metal staple in each vertebra.

A staple of "saddle" of such a size as to fit snugly over the vertebra is first selected and driven into place over the vertebra. A screw is then passed through a hole in the staple and into the vertebra until only the head of the screw protrudes above the staple. A metal cable is passed through a hole in the head of the screw. The procedure is repeated on successive vertebrae with a single cable being passed through all screw heads. Tension is applied to the cable, to obtain the necessary corrective force. The tension may be applied one stage at a time, after the cable has been passed through each respective screw-head, or it may be applied after the cable has been passed through several or all of the screw-heads. When the correct tension has been obtained, the screw-head is crimped over the cable so as to maintain the cable at the necessary tension.

The present invention relates to a surgical instrument, which is a tensioner designed specifically for applying the necessary tension to the metal cable to straighten the spinal column.

The present invention provides a surgical instrument having two handles hinged together at a main hinge, each handle having an extension beyond the hinge so arranged that movement about the hinge of the two handles toward one another causes the two extensions to move away from one another, wherein one extension has, at the end remote from the hinge, cable receiving means consisting essentially of a bifurcated arm defining a slot open at one end to receive a cable, and wherein the second extension has, at the end remote from the hinge, two jaws between which a metal cable can be gripped, the instrument having means to ensure that movement together of the two handles causes the jaws, if open, to close and movement away from one another of the two handles causes the jaws, if closed, to open prior to causing any movement of the two extensions relative to one another.

The second extension may terminate in a first member provided, at the end remote from the main hinge, with one of the jaws, and the second extension also includes a second member which is slidable with respect to the said first member and is provided, at the end remote from the main hinge, with the second jaw, wherein the said second member is coupled to the second handle, which has a pivot at a point along its length between the main hinge and the point of coupling of the said second member.

Advantageously, the axis of the pivot and the axis of the main hinge are substantially parallel. Advantageously, also, the plane in which the first jaw lies is parallel to that in which the second jaw lies irrespective of whether the jaws are open or closed. Moreover, advantageously, the said two planes are parallel to the axis of the pivot and/or parallel to the axis of the main hinge irrespective of the positions of the jaws and of the relative positions of the handles.

The second extension preferably terminates in a hollow cylinder (the said first member) the end remote from the main hinge of which serves as the first jaw, with the second jaw attached to the end of a shaft (the said second member) which is moveably contained within the cylinder and is coupled to the second handle. When the handles are moved apart, the shaft is caused to move in the direction of the end of the cylinder remote from the main hinge, thus pushing the second jaw away from the first jaw. When the handles are moved together, the shaft is pulled in the opposite direction and the jaws close. A first jaw faces in a direction away from the second handle, and the second jaw faces in the opposite direction.

Preferably, when the jaws are apart, the shaft can be rotated within the cylinder thus moving the first jaw in relation to the second jaw. This may be achieved with a number of structures known in the prior art, e.g. see U.S. Pat. Nos. 462,829; 718,306 or 3,424,027. In this way the tensioner can be adapted for either right-hand or left-hand use.

The cylinder is preferably, at the end remote from the main hinge, bifurcated, with the end surfaces of the two branches serving as the first jaw. Preferably also, a lug is secured to the shaft, which lug is accommodated in a slot between the two branches of the bifurcated cylinder, when the two jaws are closed. If the shaft can be rotated as described above, this lug can advantageously be accommodated in either slot between the two branches of the cylinder.

The end of the shaft or other second member nearer the main hinge is advantageously pivotably joined to one end of a coupling member, the other end of which is pivotably joined to the second handle or, preferably, to a short side arm provided on the second handle. Preferably, the axes of the said two pivots are parallel to one another, and preferably also parallel to the axis of the main hinge.

A screw-threaded shaft may be attached to the end of one handle and passed through the end of the other handle, with a nut, preferably a knurled nut, provided on the shaft such that it can be screwed along the shaft so as to apply pressure to push the handles together.

Various forms of tensioners according to the invention will now be described, by way of example only, with reference to the accompanying drawings, in which:

FIG. 2 is a perspective view of a slightly modified form of the second extension of the tensioner shown in FIG. 1;

FIG. 3 is a perspective view of the extension shown in FIG. 2 but from the opposite side;

FIG. 4 is a cross-section through the extension shown in FIGS. 2 and 3 with the jaws apart;

FIG. 5 is a similar view to that of FIG. 4 but with the jaws closed; and

FIG. 6 is a perspective view showing the screw-threaded shaft and the ends of the two handles, in a form slightly different from that of FIG. 1.

Figure 1:
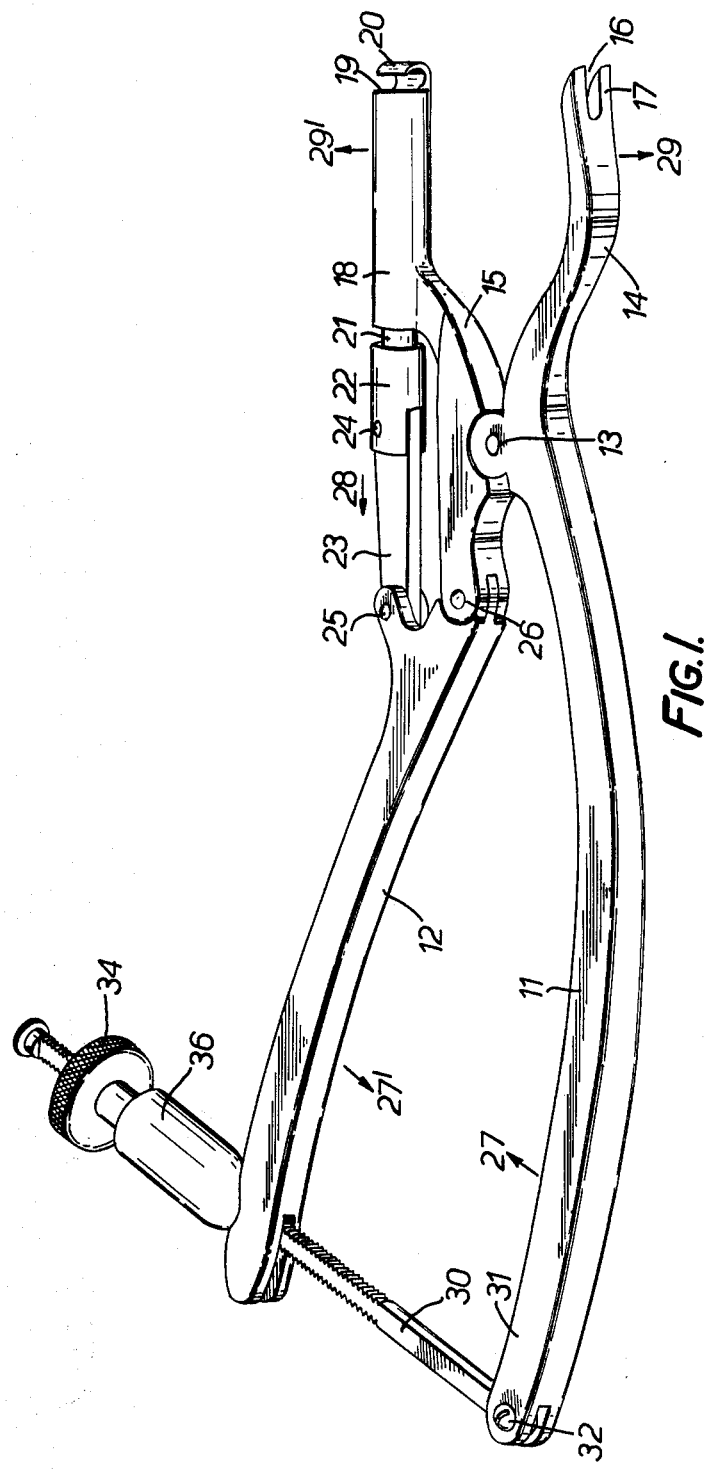
FIG. 1 is a perspective view of one form of tensioner according to the invention.

The tensioner is made of stainless steel. It has two handles 11, 12 which are hinged together at a main hinge 13. Each handle has an extension 14, 15 respectively beyond the hinge 13. The first extension 14 has at its end an open-ended slot 16 to receive a cable and a surface 17 to operate against the surface from which the cable protrudes. The second extension 15 terminates in a cylinder 18, the end of which remote from the hinge 13 serves as a first jaw 19. A second jaw 20 is attached to a shaft 21 contained within the cylinder 18 and coupled via coupling members 22, 23 and pivots 24, 25 to a short side arm provided on the handle 12. The handle 12 is pivoted at 26 between pivot 25 and hinge 13. When the handles 11, 12 are moved together as shown by arrows 27, 27', the handle 12 moves about the hinge 26 thus pulling the coupling members 22, 23 and the shaft 21 in the direction 28 and closing the jaws 19, 20 against one another. When the two jaws 19, 20 are closed no further rotational movement is possible about the hinge 26, and the handle 12 rotates relative to the handle 11 about the hinge 13 thus moving the two extensions 14, 15 away from one another as shown by the arrows 29, 29'. With the surface 17 abutting the surface from which a cable protrudes, and with the cable passing through the slot 16 and being gripped between the jaws 19, 20, tension can be applied to the cable by moving the handles 11, 12 together.

Normally, the surface against which the surface 17 operates will be the head of a spinal screw. The screw will have been secured through a spinal staple into a vertebra, and a metal cable will have been passed through a hole in the screw-head. Tension is applied to the cable as described above, and then the head of the screw can be crimped over the cable so as to maintain it at the desired tension. The process can be repeated with screws in subsequent vertebrae one at a time; alternatively tension can be applied over several vertebrae at once.

A partially screw-threaded shaft 30 of rectangular cross-section is hinged at the end 31 of the handle 11 about hinge 32. This shaft 30 passes through a slot in the end of the handle 12. A knurled nut 34 is provided on the shaft and this can be screwed along the shaft to operate against a spring 35 (no visible in FIG. 1; see FIG. 6), which in turn operates against the inside of a partially dome-shaped hollow collar 36. This collar 36 in turn operates against the handle 12 to move it in the direction 27'. The handles 11, 12 can alternatively be moved together by manual pressure.

FIG. 2 to 5 show a slightly modified form of the extension 15 of FIG. 1. As in FIG. 1, the extension terminates in a cylinder 18, the end remote from the hinge 13 of which serves as a jaw 19. The second jaw 20 is attached to a shaft 21 contained within the cylinder and this shaft 21 is attached to a coupling member 22. The end of the cylinder 18 is bifurcated and there are two opposed slots 37, 38 each capable of receiving a lug 39 secured to the shaft 21. When the two jaws 19, 20 are wide apart, as shown in FIGS. 2 to 4, the shaft 21 can be rotated within the cylinder 18 and relative to the coupling member 22, so as to align the lug 39 either with the slot 37 or with the opposed slot 38. When the jaws 19, 20 are closed, as shown in FIG. 5, the lug 39 is retracted into one of the slots 37, 38 (slot 38 in FIG. 5) and thus the shaft 21 is prevented from rotating. This rotational movement of the shaft 21 permits a choice of direction for the opening between the jaws 19, 20, and thus the tensioner can be adapted for either right-hand or left-hand use. The jaws 19, 20 are provided with respective slots 40, 41 for receiving the cable.

Various surgical implants for use in the Dwyer technique of anterior instrumentation of the spine are described and claimed in the complete specifications accompanying U.K. Patent applications Nos. 17610/75, 17611/75, and 17612/75.

What I claim is:

1. A surgical instrument for applying tension to a cable for straightening a spinal column, said instrument having first and second handles hinged together at a main hinge, each handle having an extension beyond the hinge so arranged that movement about the hinge of the two handles toward one another causes the two extensions to move away from one another, wherein one extension has, at the end remote from the hinge, cable receiving means consisting essentially of a bifurcated arm defining a slot open at one end to receive a cable, and wherein the second extension has, at the end remote from the hinge, two jaws between which a metal cable can be gripped, the instrument having means to ensure that movement together of the two handles causes the jaws, if open, to close and movement away from one another of the two handles causes the jaws, if closed, to open prior to causing any movement of the two extensions relative to one another.

2. An instrument as claimed in claim 1, wherein the second extension terminates in a first member provided, at the end remote from the main hinge, with one of the jaws, and the second extension also includes a second member which is slidable with respect to the said first member and is provided, at the end remote from the main hinge, with the second jaw, wherein the said second member is coupled to the second handle, which has a pivot at a point along its length between the main hinge and the point of coupling of the said second member.

3. An instrument as claimed in claim 2, wherein the axis of the pivot and the axis of the main hinge are substantially parallel.

4. An instrument as claimed in claim 3, wherein the plane in which the first jaw lies is parallel to that in which the second jaw lies irrespective of whether the jaws are open or closed.

5. An instrument as claimed in claim 4, wherein the said two planes are parallel to the axis of the pivot and to the axis of the main hinge irrespective of the positions of the jaw and of the relative positions of the handles.

6. An instrument as claimed in claim 2 wherein the second extension terminates in a hollow cylinder, which constitutes the said first member, the end remote from the main hinge of which cylinder serves as the first jaw with the second jaw attached to the end of a shaft, which constitutes the said second member, moveably contained within the cylinder and coupled to the second handle.

7. An instrument as claimed in claim 6, wherein, when the jaws are apart, the shaft can be rotated within the cylinder.

8. An instrument as claimed in claim 6, wherein the cylinder is, at the end remote from the main hinge, bifurcated, with the end surfaces of the two branches of the bifurcated cylinder serving as the first jaw.

9. An instrument as claimed in claim 8, wherein a lug is secured to the shaft, which lug, when the jaws are closed, is accommodated in a slot between the two branches of the bifurcated cylinder.

10. An instrument as claimed in claim 1, wherein the proximal end of the second member nearer the main hinge is pivotably joined to one end of a coupling member, the distal end of which is pivotally joined to the second handle.

11. An instrument as claimed in claim 10, wherein the axes of the said two pivots are parallel to one another and to the axis of the main hinge.

12. An instrument as claimed claim 1, wherein a screw-threaded shaft is attached to the end of one handle and can be passed through the end of the other handle, with a nut so arranged on the shaft that it can be screwed along the shaft so as to apply pressure to push the handles together.

13. An instrument as claimed in claim 10, wherein the distal end of said coupling member is joined to the second handle via a short side arm provided on the second handle.

* * * * *